United States Patent
Ruppert et al.

(10) Patent No.: US 7,805,176 B2
(45) Date of Patent: Sep. 28, 2010

(54) EXCHANGE-WEIGHTED XENON-129 NUCLEAR MAGNETIC RESONANCE SYSTEM AND RELATED METHOD

(75) Inventors: Kai Ruppert, Havertown, PA (US); John P. Mugler, III, Charlottesville, VA (US); James R. Brookeman, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 730 days.

(21) Appl. No.: 10/592,200

(22) PCT Filed: Mar. 9, 2005

(86) PCT No.: PCT/US2005/008059

§ 371 (c)(1),
(2), (4) Date: Sep. 8, 2006

(87) PCT Pub. No.: WO2005/086932

PCT Pub. Date: Sep. 22, 2005

(65) Prior Publication Data

US 2007/0225592 A1    Sep. 27, 2007

Related U.S. Application Data

(60) Provisional application No. 60/551,884, filed on Mar. 10, 2004.

(51) Int. Cl.
*A61B 5/05* (2006.01)
(52) U.S. Cl. .................. 600/407; 600/409; 600/410
(58) Field of Classification Search .......... 600/420, 600/431; 424/9.3
See application file for complete search history.

(56) References Cited

U.S. PATENT DOCUMENTS 4,906,932 A * 3/1990 Ordidge ............... 324/309

(Continued)

FOREIGN PATENT DOCUMENTS

WO    WO 01/67955    9/2001

(Continued)

OTHER PUBLICATIONS

Abraham M.H., "Solubility Properties in Polymers and Biological Media. 2. The Correlation and Prediction of the Solubilities of Nonelectrolytes in Biological Tissues and Fluids", Journal of Medicinal Chemistry, 1985, p. 865-870, vol. 28, Issue 7.

(Continued)

*Primary Examiner*—Long V Le
*Assistant Examiner*—Joel F Brutus
(74) *Attorney, Agent, or Firm*—Robert J. Decker; Blank Rome LLP

(57) ABSTRACT

Method and system that provides, among other things, the capability for using hyperpolarized xenon-129 as a probe to non-invasively and non-destructively characterize important properties of certain structures or materials into which hyperpolarized xenon-129 can be introduced and wherein the xenon exists in two or more chemically-shifted states that are in exchange High-resolution MR images can be generated in a fraction of a second wherein the associated signal intensities reflect material properties that characterize the gas exchange among the different states. For example, in the human or animal lung, the system and related method can exploit the differences in gas-exchange characteristics between healthy and diseased lung tissue to generate high-resolution, high signal-to-noise cross-sectional MR images that permit non-invasive regional detection of variations in lung tissue structure with a combination of spatial and temporal resolution that is unmatched by any current imaging modality.

34 Claims, 3 Drawing Sheets

U.S. PATENT DOCUMENTS

| | | | |
|---|---|---|---|
| 5,245,282 | A | 9/1993 | Mugler |
| 5,485,086 | A | 1/1996 | Meyer |
| 5,492,123 | A | 2/1996 | Edelman |
| 5,545,396 | A | 8/1996 | Albert |
| 5,565,776 | A | 10/1996 | Kanazawa |
| 5,604,435 | A | 2/1997 | Foo |
| 5,671,741 | A | 9/1997 | Lang |
| 5,749,834 | A | 5/1998 | Hushek |
| 5,785,953 | A | 7/1998 | Albert |
| 5,789,921 | A | 8/1998 | Albert |
| 6,230,039 | B1 | 5/2001 | Stuber |
| 6,241,966 | B1 | 6/2001 | Albert |
| 6,281,681 | B1 | 8/2001 | Cline |
| 6,426,058 | B1 | 7/2002 | Pines |
| 6,491,895 | B2 | 12/2002 | Driehuys |
| 6,630,126 | B2 | 10/2003 | Driehuys |
| 6,775,568 | B2 | 8/2004 | Mugler |
| 7,164,268 | B2 | 1/2007 | Mugler |
| 7,174,200 | B2 | 2/2007 | Salerno |
| 2001/0041834 | A1* | 11/2001 | Mugler et al. ............... 600/420 |
| 2007/0197903 | A1 | 8/2007 | Mugler, III et al. |

FOREIGN PATENT DOCUMENTS

| | | |
|---|---|---|
| WO | WO 02/50574 | 6/2002 |
| WO | WO 02/084305 | 10/2002 |
| WO | WO 03/098390 | 11/2003 |
| WO | WO 2005/086931 | 9/2005 |

OTHER PUBLICATIONS

Albert, M.S., "Biological Magnetic Resonance Imaging Using Laser-Polarized 129Xe", Nature, 1994, p. 199-201, vol. 370.

Altes, T.A., "Hyperpolarized 3He MR Lung Ventilation Imaging in Asthmatics: Preliminary Findings", Journal of Magnetic Resonance Imaging, 2001, p. 378-384, vol. 13, Issue 3.

Black, R.D., "In vivo He-3 MR Images of Guinea Pig Lungs", Radiology, 1996, p. 867-870, vol. 199, No. 3.

Chen, X.J., "Detection of Emphysema in Rat Lungs by Using Magnetic Resonance Measurements of 3He Diffusion", Proceedings of the National Academy of Sciences of the United States of America, 2000, p. 11478-11481, vol. 97, No. 21.

Chen, X.J., "Spatially Resolved Measurements of Hyperpolarized Gas Properties in the Lung in Vivo. Part I: Diffusion Coefficient", Magnetic Resonance in Medicine, 1999, p. 721-728, vol. 42, Issue 4.

De Lange, E.E., "Lung Air Spaces: MR Imaging Evaluation with Hyperpolarized 3He Gas", Radiology, 1999, p. 851-857, vol. 210, No. 3.

Donnelly, L.F., "Cystic Fibrosis: Combined Hyperpolarized 3He-enhanced and Conventional Proton MR Imaging in the Lung—Preliminary Observations", Radiology, 1999, p. 885-889, vol. 212, No. 3.

Gurney, J.W., "Pathophysiology of Obstructive Airways Disease", Radiologic Clinics of North America, 1998, p. 15-27, vol. 36, No. 1.

Kauczor, H.U., "Imaging of the Lungs using 3He MRI: Preliminary Clinical Experience in 18 Patients with and without Lung Disease", Journal of Magnetic Resonance Imaging, 1997, p. 538-543, vol. 7, No. 3.

Kauczor, H.U., "Normal and Abnormal Pulmonary Ventilation: Visualization at Hyperpolarized He-3 MR Imaging", Radiology, 1996, p. 564-568, vol. 201, No. 2.

MacFall, J.R., "Human Lung Air Spaces: Potential for MR Imaging with Hyperpolarized He-3", Radiology, 1996, p. 553-558, vol. 200, No. 2.

Middleton, H., "MR Imaging with Hyperpolarized He-3 Gas", Magnetic Resonance in Medicine, 1995, p. 271-275, vol. 33, Issue 2.

Miller, K.W., "Xenon NMR: Chemical Shifts of a General Anesthetic in Common Solvents, Proteins, and Membranes", Proceedings of the National Academy of Sciences of the United States of America, 1981, p. 4946-4949, vol. 78, No. 8.

Moseley, M.E., "Early Detection of Regional Cerebral Ischemia in Cats: Comparison of Diffusion- and T2-weighted MRI and Spectroscopy", Magnetic Resonance in Medicine, 1990, p. 330-346, vol. 14, Issue 2.

Mugler, J.P. III, "Regional Measurement of the 3He Diffusion Coefficient in the Human Lung", Proceedings of the International Society for Magnetic Resonance in Medicine, 6th Meeting, 1998, p. 1906, Issue S1.

Mugler, J.P. III, "The Apparent Diffusion Coefficient of Xe-129 in the Lung: Preliminary Human Results", Proceedings of the International Society for Magnetic Resonance in Medicine, 12th Meeting, 2004, p. 769, Kyoto, Japan.

Ruppert, K., "Probing Lung Physiology with Xenon Polarization Transfer Contrast (XTC)", Magnetic Resonance in Medicine, 2000, p. 349-357, vol. 44, Issue 3.

Ruppert, K., "Exploring Lung Function with Hyperpolarized 129Xe Nuclear Magnetic Resonance", Magnetic Resonance in Medicine, 2004, p. 676-687, vol. 51, Issue 4.

Saam, B.T., "MR Imaging of Diffusion of 3He Gas in Healthy and Diseased Lungs", Magnetic Resonance in Medicine, 2000, p. 174-179, vol. 44, Issue 2.

Salerno, M., "Emphysema: Hyperpolarized Helium 3 Diffusion MR Imaging of the Lungs Compared with Spirometric Indexes—Initial Experience", Radiology, 2002, p. 252-260, vol. 222, No. 1.

Song, Y.Q., "Spin-Polarized 129Xe Gas Imaging of Materials", Journal of Magnetic Resonance, 1995, p. 127-130, Series A 115.

Takasugi, J.E., "Radiology of Chronic Obstructive Pulmonary Disease", Radiologic Clinics of North America, 1998, p. 29-55, vol. 36, No. 1.

Van Beek, "Assessment of Lug Ventilation by MR Imaging: Current Status and Future Perpectives", European Radiology, 2002, p. 1962-1970, vol. 12, Springer-Verlag.

Walker, T.G., "Spin-Exchange Optical Pumping of Noble Gas Nuclei", Reviews of Modern Physics, 1997, p. 629-642, vol. 69, No. 2.

Yablonskiy, D.A., "Quantitative in Vivo Assessment of Lung MicroStructure at the Alveolar Level with Hyperpolarized 3He Diffusion MRI", Proceedings of the National Academy of Sciences of the United States of America, 2002, p. 3111-3116, vol. 99, No. 5.

* cited by examiner

EXCHANGE-WEIGHTED XENON-129 NUCLEAR MAGNETIC RESONANCE SYSTEM AND RELATED METHOD

CROSS-REFERENCE TO RELATED APPLICATIONS

This application is a national stage filing of International Application No. PCT/US2005/008059, filed Mar. 9, 2005, which claims priority from U.S. Provisional Application No. 60/551,884, filed on Mar. 10, 2004, entitled "Exchange-Weighted Xenon-129 Nuclear Magnetic Resonance System and Related Method," the disclosures of which are hereby incorporated by reference in their entirety.

The present application is also related to PCT International Application No. PCT/US05/008058, filed Mar. 9, 2005 (which claimed priority to Provisional Application No. 60/551,877), entitled "System and Method for Improved Detection and Assessment of Changes in Lung Tissue Structure," of which are assigned to the present assignee and are hereby incorporated by reference herein in their entirety. The present invention may be implemented with the technology discussed throughout the aforementioned International Application entitled "System and Method for Improved Detection and Assessment of Changes in Lung Tissue Structure."

FIELD OF THE INVENTION

The present invention relates generally to magnetic resonance imaging or spectroscopy, and more particularly to using the signal from hyperpolarized xenon-129 ("Xe129") nuclei in one compartment to indirectly measure characteristics of xenon-129 nuclei in one or more other compartments which resonate at a frequency or frequencies distinct from that of the first compartment and which exchange in some manner with the nuclei of the first compartment.

BACKGROUND OF THE INVENTION

Over the past twenty years, nuclear magnetic resonance imaging (MRI) has developed into an important modality for both clinical and basic-science imaging applications. Nonetheless, advancements continue at a rapid pace. A recent notable advance was the introduction of "hyperpolarized" noble gases as new contrast agents [1]. Under typical experimental conditions, the nuclear polarization for MRI (to which the signal level, or in more general terms, the image quality, is proportional) is at most on the order of $10^{-4}$, whereas polarizations approaching 100% are possible with hyperpolarized gases. Therefore, considering that in general nuclear magnetic resonance (NMR) is inherently limited by the available signal-to-noise ratio, hyperpolarized gases present the possibility for applications that were heretofore not feasible.

Of particular interest for hyperpolarized-gas NMR studies are the two non-radioactive noble-gas isotopes with a nuclear spin of 1/2, helium-3 and xenon-129. Both nuclei are useful for imaging of gas-filled spaces, such as cracks and voids in materials [2], or the lungs and sinuses in humans and animals [1]. Xenon-129 is soluble in a variety of substances, while helium-3 in general has a very low solubility [3]. In particular, xenon is lipophilic, having a high solubility in oils and lipid-containing tissues. Another important characteristic of xenon-129 is an exquisite sensitivity to its environment that results in an enormous range of chemical shifts upon solution (e.g., a range of approximately 200 ppm in common solvents) or adsorption [4]. These solubility and chemical shift characteristics make xenon-129 a valuable probe for a variety of material science and biological applications.

The behavior of xenon when inhaled by a human or an animal is a particularly interesting and important example to consider. Inhaled xenon dissolves rapidly into the bloodstream and is transported throughout the body, with preferential distribution to lipid-rich regions. Thus, dissolved-phase MRI of hyperpolarized xenon-129 may allow perfusion imaging of the brain, lung, and other organs, and offers the potential for the non-invasive characterization of other important physiological parameters. Although direct, high-resolution, dissolved-phase in-vivo MR imaging of xenon-129, particularly in humans, has remained elusive, the xenon polarization transfer contrast (XTC) MRI technique [5] has provided the means to generate high-resolution MR images of gaseous xenon-129 whose contrast reflects the characteristics of xenon gas-exchange between gas and dissolved-phase compartments. For example, in the lung, XTC MRI takes advantage of the rapid gas exchange between the lung parenchyma and the alveolar airspaces, and the large chemical-shift difference between dissolved and gaseous xenon, to manipulate the dissolved-phase magnetization by using radio-frequency pulses and subsequently observe the changes in the gas-phase magnetization. Depending on the pulse-sequence parameters that are chosen, the resulting gas-depolarization maps can be made to reflect various lung physiological parameters such as the lung tissue volume, the alveolar surface-to-volume ratio or the blood volume in the alveolar capillary beds [6].

Despite the inherent flexibility of XTC MRI and its potential for yielding, for example in the lung, information of physiological and medical relevance, the technique provides suboptimal sensitivity due to the relatively low signal-to-noise ratio and the low temporal resolution (several seconds) for the implementations that have been developed to date. Thus, it would be highly desirable to develop an MR technique that generates high-resolution images, whose contrast reflects gas-exchange properties as is possible with XTC MRI, but that also yields a much higher signal-to-noise ratio and sub-second temporal resolution.

BRIEF SUMMARY OF INVENTION

An aspect of an embodiment of the present invention comprises the methodology and system for using the signal from hyperpolarized xenon-129 nuclei in one compartment, which resonate at a given frequency determined by their chemical shift and the strength of the applied magnetic field of the NMR or MRI system, to indirectly measure, using MR spectroscopy or imaging methods, characteristics, such as the concentration, of xenon-129 nuclei in one or more other compartments which resonate at a frequency or frequencies distinct from that of the first compartment and which exchange in some manner with the nuclei of the first compartment.

For example, the first compartment could be gas-phase hyperpolarized xenon in the lung air spaces and the other compartments could be dissolved-phase hyperpolarized xenon in the lung parenchyma and in the blood of the alveolar capillary bed. For this example, an embodiment of the present invention provides the means, among other possibilities, to acquire high-resolution magnetic resonance images of the gas-phase xenon that reflect the concentration of the dissolved-phase xenon. With an appropriate choice of parameter values, the gas-phase images thusly created indicate the regional volume of lung parenchyma, an important physiological parameter of medical relevance. In essence, the invention permits the strong xenon gas-phase signal to be used as an amplifier to measure, rapidly and with high spatial resolution, characteristics of the much weaker xenon dissolved-phase signal by taking advantage of the exchange that occurs between the gas and dissolved phases. This embodiment of the present invention thus provides the means to map, in a non-invasive and practical fashion, various properties of the lung that cannot be mapped non-invasively at a competitive resolution, speed and signal-to-noise ratio by any other method.

An aspect of an embodiment of the present invention provides a method for characterizing properties of a certain structure or material, wherein the structure or material have at least one compartment therein. At least one of the compartments define at least one reference compartment, and the structure or material also has at least one other compartment, which defines at least one target compartment. The method comprises: a) introducing hyperpolarized xenon-129 gas in the structure or material and placing the structure or material in a NMR or MRI system; b) creating transverse magnetization from the hyperpolarized xenon-129 gas in at least one of the reference compartments that has a corresponding chemical shift; and c) leaving the NMR or MRI system unperturbed for an appropriately chosen delay time. The delay time may be chosen such that a sufficiently large quantity of xenon-129 atoms enters the target compartments from the reference compartment. The xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process. Upon return to the reference compartment the transverse magnetization is dephased relative to that which remained in the reference compartment and this transverse magnetization from the target compartments thus makes a reduced contribution to the coherent gas-phase signal, which results in a reduced net signal from the alveolar gas-phase transverse magnetization compared to the situation wherein there is relatively reduced or no xenon exchange between the reference and target compartments. The method may also include measuring the signal from hyperpolarized xenon-129 in the reference compartment.

An aspect of an embodiment of the present invention provides a system for characterizing properties of a certain structure or material, wherein the structure or material may have at least one compartment therein. At least one of the compartment define at least one reference compartment, and the structure or material also has at least one other compartment therein, which defines at least one target compartment. Accordingly, the system comprises an NMR or MRI system where it is adapted to allow the introduction of hyperpolarized xenon-129 gas in the structure or material and placement of the structure or material in the NMR or MRI system. Additionally, the NMR or MRI system may be adapted to allow creation of transverse magnetization from the hyperpolarized xenon-129 gas in at least one of the reference compartments that has a corresponding chemical shift. Further, the NMR or MRI system may be adapted to allow its system to be unperturbed for an appropriately chosen delay time. The delay time may be chosen such that a sufficiently large quantity of xenon-129 atoms enters the target compartments from the reference compartment, the xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process. Further, upon return to the reference compartment the transverse magnetization is dephased relative to that which remained in the reference compartment and this transverse magnetization from the target compartments thus makes a reduced contribution to the coherent gas-phase signal, which results in a reduced net signal from the alveolar gas-phase transverse magnetization compared to the situation wherein there is relatively reduced or no xenon exchange between the reference and target compartments. Still further, the NMR or MRI system may be adapted to allow for the measurement of the signal from hyperpolarized xenon-129 in the reference compartment.

Besides the lung, the various embodiments of the present invention also have application to the study and characterization of certain materials wherein hyperpolarized xenon introduced into or surrounding the material exists in distinct, chemically-shifted environments that are in exchange.

These and other objects, along with advantages and features of the invention disclosed herein, will be made more apparent from the description, drawings and claims that follow.

BRIEF SUMMARY OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF THE INVENTION

Figure 1:
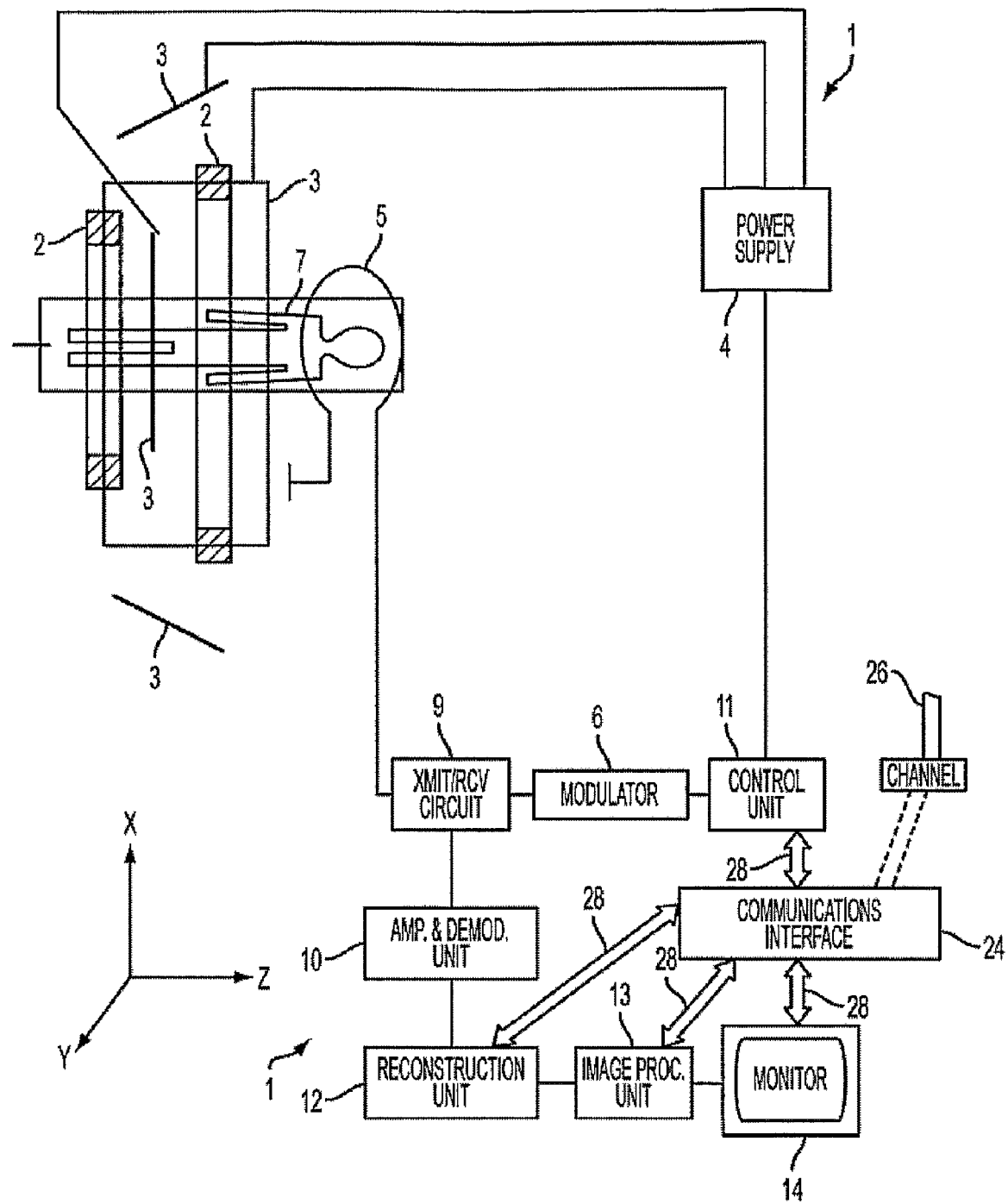
FIG. 1 illustrates a simplified exemplary embodiment of a MRI apparatus for practicing the present invention. The present invention method can be applied to various commercially available MRI apparatuses.

Various embodiments of the present invention apply to, but are not limited thereto, the situation wherein there is a structure or material into or around which hyperpolarized xenon-129 can be introduced and wherein said xenon-129 exists in two or more chemically-shifted states that are in exchange, either directly or indirectly, within a time frame similar to or less than the characteristic NMR time constants for xenon in the given structure or material. For example, for purposes of this document, we define the "hyperpolarized" state as a large (relative to the thermal equilibrium polarization for xenon-129 in the applied static magnetic field), non-equilibrium nuclear polarization created by any method, including, but not limited to, optical pumping and spin exchange [7]. Given such a structure or material containing hyperpolarized xenon-129, placed in a suitable NMR or MRI system, this embodiment of the present invention can be summarized by the following three-step process:

1. Using an appropriate MR spectroscopy or imaging method, transverse magnetization from hyperpolarized xenon-129 in at least one compartment (which we will term the reference compartment) with a corresponding chemical shift, is created.
2. The system is left unperturbed for an appropriately chosen delay time. The duration of this delay is determined by the strength of the external magnetic field, the exchange rate between the reference compartment and the other compartments (which we will term the target compartments) and the xenon-129 diffusion properties in the target compartments. The delay time is chosen such that a sufficiently large quantity of xenon-129 atoms enter the target compartments from the reference compartment, the xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment. (The phase shift acquired is directly proportional to the residence time within the target compartment. Due to the random nature of the process, a population of xenon-129 atoms will experience a range of residence times and hence a range of phase shifts.) Upon return to the reference compartment the transverse magnetization is dephased relative to that which remained in the reference compartment and this transverse magnetization from the target compartments thus makes a reduced contribution to the coherent gas-phase signal, which results in a reduced net signal from the alveolar gas-phase transverse magnetization compared to the situation wherein there is relatively reduced or no xenon exchange between the reference and target compartments.
3. Using an appropriate MR spectroscopy or imaging method, the signal from hyperpolarized xenon-129 in the reference compartment is measured. The signal from the reference compartment now reflects the degree of dephasing of the xenon-129 transverse magnetization inside the target compartments with respect to the reference compartment (step 2), and the time constants, partition coefficients and geometrical factors characterizing the xenon exchange between the reference and target compartments. Specifically, the information (e.g., volume of material in which the xenon dissolves) that the measured signal reflects depends on the difference in resonance frequency between the reference and the target compartments. The signal from hyperpolarized xenon-129 in the reference compartment at this step may also reflect other independent processes such as T1 and T2 relaxation, and diffusion of xenon in the reference compartment. However, by choosing an appropriate delay time and an appropriately designed pulse sequence, one can ensure that these other contributions are insignificant relative to that from the exchange process. The resulting signal thus primarily reflects characteristics of the xenon-exchange process or, in other words, is "exchange weighted."

FIG. 1 illustrates a simplified schematic of a MR apparatus 1 or scanner or spectrometer for practicing an embodiment of the present invention. The MR apparatus 1 includes a main magnet system 2 for generating a steady magnetic field in an examination zone(s) of the MR apparatus. The z-direction of the coordinate system illustrated corresponds to the direction of the steady magnetic field generated by the magnet system 2.

The MR system, scanner or spectrometer also includes a gradient magnet system 3 (optional for the spectrometer) for generating temporary magnetic fields $G_x$, $G_y$ and $G_z$ directed in the z-direction but having gradients in the x, y or z directions, respectively. With this magnetic gradient system, magnetic-field gradients can also be generated that do not have directions coinciding with the main directions of the above coordinate system, but that can be inclined thereto, as is known in the art. Accordingly, the present invention is not limited to directions fixed with respect to the MR system.

Also, while traditional commercial methods provide linear gradients in the x, y, or z directions it is also possible not to utilize all three of these linear gradients. For example, rather than using a linear z gradient, one skilled in the art can use a z-squared dependence or some other spatial dependence to provide desired results.

The magnet systems 2 and 3 enclose an examination zone(s) which is large enough to accommodate a part of an object 7 to be examined, for example a part of a human patient. A power supply means 4 feed the gradient magnet system 3.

The MR system also includes an RF transmitter system including RF transmitter coil 5, which generates RF pulses in the examination zone and is connected via transmitter/receiver circuit 9 to a RF source and modulator 6.

The RF transmitter coil 5 is arranged around the part of body 7 in the examination zone. The MR apparatus also comprises an RF receiver system including an RF receiver coil which is connected via transmitter/receiver circuit 9 to signal amplification and demodulation unit 10. The receiver coil and the RF transmitter coil 5 may be one and the same coil.

A gas supply (and/or gas regulator), not shown, provides hyperpolarized Xe129 gas to the examination zone or region of the object/subject (body, cavity, or the like). The gas supply may be an attachable supply line to the object/subject or may be a portable gas supply such as a container, bolus delivery device, or dose bag. As would be appreciated by one skilled in the art, there are wide variety of methods and systems adapted for supplying hyperpolarized gas to the object or subject (or region and examination zone). For illustrative examples of magnetic resonance imaging that may or may not use hyperpolarized gases include the following patents and patent applications and are hereby incorporated by reference herein in their entirety: 1) commonly assigned U.S. Pat. No. 5,245,282, filed Jun. 28, 1991, entitled "Three-dimensional Magnetic Resonance Imaging," 2) co-assigned U.S. Pat. No. 6,630,126 B2, filed Mar. 12, 2001, entitled "Diagnostic Procedures Using Direct Injection of Gaseous Hyperpolarized 129Xe and Associated Systems and Products," and its corresponding International Patent Application Serial No. PCT/US01/07812, filed Mar. 12, 2001 (Publication No.: WO/01/67955 A2), 3) co-assigned U.S. Pat. No. 6,775,568 B2, filed Apr. 12, 2001, entitled "Exchange-Based NMR Imaging and Spectroscopy of Hyperpolarized Xenon-129," 4) pending and commonly assigned U.S. patent application Ser. No. 10/451,124, filed Jun. 19, 2003, entitled "Method and Apparatus for Spin-echo-train MR Imaging Using Prescribed Signal Evolutions" and corresponding International Patent Application Serial No. PCT/US01/50551, filed Dec. 21, 2001, entitled "Method and Apparatus for Spin-echo-train MR Imaging Using Prescribed Signal Evolutions," 5) pending and commonly assigned U.S. patent application Ser. No. 10/474,571, filed Oct. 14, 2003, entitled "Optimized High Speed Magnetic Resonance Imaging Method and System Using Hyperpolarized Noble Gases" and corresponding International Patent Application Serial No. PCT/US02/11746, filed Apr. 12, 2002, entitled "Optimized High Speed Magnetic Resonance Imaging Method and System Using Hyperpolarized Noble Gases," and 6) pending and commonly assigned International Patent Application Serial No. PCT/US03/151136, filed May 14, 2003, entitled "Method and System for Rapid Magnetic Resonance Imaging of Gases with Reduced Diffusion-induced Signal Loss."

Some illustrative examples of magnetic resonance imaging that may or may not use hyperpolarized gases are provided in the following patent applications and patents and are hereby incorporated by reference herein in their entirety: U.S. Pat. No. 5,545,396 to Albert et al., entitled "Magnetic Resonance Imaging Using Hyperpolarized Noble Gases;" U.S. Pat. No. 5,785,953 to Albert et al., entitled "Magnetic Resonance Imaging Using Hyperpolarized Noble Gases;" and U.S. Pat. No. 5,789,921 to Albert et al., entitled "Magnetic Resonance Imaging Using Hyperpolarized Noble Gases." Some aspects of some embodiments of the present invention may be implemented with the technology discussed in U.S. Pat. No. 6,491,895 B2 to Driehuys et al., entitled "Method for Imaging Pulmonary and Cardiac Vasculature and Evaluating Blood Flow Using Dissolved Polarized XE129," U.S. Pat. No. 5,492,123 to Edelman, entitled "Diffusion Weighted Magnetic Resonance Imaging," Pines et al., U.S. Pat. No. 6,426,058 B1, entitled "Enhancing of NMR and MRI in the Presence of Hyperpolarized Noble Gases," and U.S. Pat. No. 6,241,966 B1 to Albert et al., entitled "Magnetic Resonance Imaging Using Hyperpolarized Noble Gases."

The MR system, scanner or spectrometer also includes an amplification and demodulation unit or system 10, which, after excitation of nuclear spins in a part of the body placed within the examination space by RF pulses, after encoding by the magnetic-field gradients (if applicable) and after reception of the resulting MR signals by the receiver coil, derives sampled phases and amplitudes from the received MR signals. An image reconstruction unit or system 12 processes the received MR signals to, inter alia, reconstruct an image or spectrum by methods well-known in the art, such as by Fourier transformation. It should be appreciated by one skilled in the art that various reconstruction methods may be employed besides the Fourier Transform (FT) depending on factors such as the type of signal being analyzed, the available processing capability, etc. For example, but not limited thereto, the present invention may employ Short-Time FT (STFT), Discrete Cosine Transforms (DCT), or wavelet transforms (WT). By means of an image processing unit or system 13, the reconstructed image or spectrum is displayed, for example, on monitor 14. Further, the image reconstruction unit or system can optionally process MR navigator signals to determine the displacement of a portion of the patient.

The MR system also includes a control unit or system 11 that generates signals for controlling the RF transmitter and receiver systems by means of a modulator 6, the gradient magnetic field system by means of the power supply means 4, an image reconstruction unit or system 12 and an image processing unit or system 13. In an exemplary embodiment, the control unit or system 11 (and other control elements in the MR system) are implemented with programmable elements, such as one or more programmable signal processors or microprocessors, communicating over busses with supporting RAM, ROM, EPROM, EEPROM, analog signal interfaces, control interfaces, interface to computer-readable media and so forth. These programmable elements are commanded by software or firmware modules loaded into RAM, EPROM, EEPROM or ROM, written according to well-known methods to perform the real-time processing required herein, and loaded from computer-readable media (or computer useable medium), such as magnetic disks or tapes, or optical disks, or network interconnections, removable storage drives, flash memory, or so forth. The present invention may be implemented using hardware, software or a combination thereof and may be implemented in one or more computer systems or processing systems, such as personal digit assistants (PDAs), for various applications, e.g., remote care and portable care practices.

In an embodiment, the control unit that directs a MR system for practicing the present invention can be implemented with dedicated electronic components in fixed circuit arrangements. In this case, these dedicated components are arranged to carry out the method described above. For example, the invention is implemented primarily in hardware using, for example, hardware components such as application specific integrated circuits (ASICs). Implementation of the hardware state machine to perform the functions described herein will be apparent to persons skilled in the relevant art(s).

In particular, the control unit commanded by its loaded software causes the generation of MR signals by controlling the application of MR pulse sequences, which comprise RF-pulses, time delays and temporary magnetic-field gradient pulses. These pulse sequences are generated according to the methods of the present invention as subsequently described, and generally include spectroscopy pulse sequences as well as 2D and 3D imaging pulse sequences and optionally navigator pulse sequences for determining the displacement of the patient or material.

Furthermore, according to alternate embodiments of the present invention, the MR system also optionally includes various other units (not illustrated) from which the state of motion of the part of the patient being imaged can be measured. These can include sensors directly indicating the instantaneous state of motion of the part of the patient being imaged, such as a chest belt for directly indicating chest displacement during respiration, or MR-active micro-coils whose position can be tracked, or optical means, or ultrasound means, or so forth. These units can also include sensors indirectly indicating the instantaneous state of motion of the part of the patient being imaged. For example, electrocardiogram and peripheral pulse sensors measure the temporal progress of the cardiac cycle, and permit inference of the actual state of motion of the heart from knowledge of cardiac displacements associated with each phase of the cardiac cycle. When these sensors are present to measure the state of motion, the control unit need not generate navigator pulse sequences.

Moreover, the control unit or system 11 may also include a communications interface 24. The communications interface 24 allows software and data to be transferred between and among, via communication path (i.e., channel) 28 the control unit or system 11, reconstruction unit or system 12, image processing unit or system 13, and monitor 14 and external devices. Examples of the communications interface 24 may include a modem, a network interface (such as an Ethernet card), a communications port, a PCMCIA slot and card, etc. Software and data transferred via communications interface 24 are in the form of signals that may be electronic, electromagnetic, optical or other signals capable of being received by communications interface 24. The signals are provided to communications interface 24 via the communications path (i.e., channel) 26. The channel 26 carries signals and may be implemented using wire or cable, fiber optics, a phone line, a cellular phone link, a RF link, IR link, Bluetooth, and other communications channels.

Some embodiments of the present invention may be implemented as software/firmware/hardware with various MR systems, and methods, as one skilled in the art would appreciate. Other exemplary systems and methods, but not limited thereto, are disclosed in the following U.S. Patents, of which are hereby incorporated by reference in their entirety herein: U.S. Pat. No. 6,281,681 B1 to Cline et al., entitled "Magnetic Resonance Imaging with Interleaved Fibonacci Spiral," U.S. Pat. No. 6,230,039 B1 to Stuber et. al., entitled "Magnetic Resonance Imaging Method and System with Adaptively Selected Flip Angles," U.S. Pat. No. 5,749,834 to Hushek, entitled "Intersecting Multislice MRI Data Acquisition Method," U.S. Pat. No. 5,656,776 to Kanazawa, entitled "Magnetic Resonance Imaging Apparatus," U.S. Pat. No. 5,604,435 to Foo et al., entitled "Spiral Scanning Method for Monitoring Physiological Changes," U.S. Pat. No. 5,485,086 to Meyer et al, entitled "Continuous Fluoroscopic MRI Using Spiral K-space Scanning," and U.S. Pat. No. 5,671,741 to Lang et al., entitled "Magnetic Resonance Imaging Technique for Tissue Characterization."

The various forms of the present invention involve using a magnetic resonance imaging or spectroscopy method/system, and more particularly to using the signal from hyperpolarized xenon-129 ("Xe129") nuclei in one compartment to indirectly measure characteristics of xenon-129 nuclei in one or more other compartments which resonate at a frequency or frequencies distinct from that of the first compartment and which exchange in some manner with the nuclei of the first compartment.

As a prerequisite, hyperpolarized Xe129 must be generated, wherein we define the "hyperpolarized" state as a large (relative to the thermal equilibrium polarization for the polarizable gas in the static magnetic field used to acquire the MR images), non-equilibrium nuclear polarization. The Xe129 may be hyperpolarized for use according to the invention through any of various means known in the art, such as spin-exchange interactions with optical pumping. See Walker T G, Happer W., "Spin-exchange Optical Pumping of Noble Gas Nuclei", Rev Mod Phys 1997; 69:629-642, of which is hereby incorporated by reference herein in its entirety. The volume and nuclear polarization of the hyperpolarized Xe129 gas are chosen based on the volume of the structure or material and on the desired spatial resolution, temporal resolution and signal-to-noise ratio of the MR signals to be generated.

In the case that the structure of interest is a lung, the lung may be that of a human or an animal, and may be in vivo or excised.

As an example, Xe129 may be introduced into the lung (for example after the subject or excised lung is positioned with an appropriate radio-frequency coil that is within an MR scanner) using any available method. This includes but is not limited to the introduction into the lung by inhalation from a plastic bag, inhalation from a computer controlled gas mixing system, introduction by depressing a gas-filled syringe, or introduction by using a computer-controlled or manually-controlled ventilation device. It may be desirable to mix other gases with the Xe129 prior to or during the inhalation process as a means to fine-tune the diffusion characteristics of the gas mixture in the lung.

A specific experimental implementation of this methodology is useful to illustrate the nature of an embodiment of the present invention. For this purpose, we will discuss the case where the reference compartment is gas-phase hyperpolarized xenon-129 in the lung air spaces of a 4-kg New Zealand rabbit and the target compartments consist of dissolved-phase hyperpolarized xenon-129 in the lung parenchyma and in the blood of the alveolar capillary bed. We compared results from a healthy rabbit to those from a rabbit that had received, over the course of 4 weeks, multiple small injections (0.15 ml) of elastase into a segmental right bronchus, mostly in the lower lobe, to induce emphysema.

Experiments were performed on a 1.5-T commercial whole-body imager (Sonata, Siemens Medical Solutions, Malvern, Pa.). The radio-frequency (RF) coil was a custom-made transmit-receive birdcage coil (IGC Medical Advances, Milwaukee, Wis.). For imaging we chose a single-shot spin-echo-train pulse sequence with a circular k-space trajectory. The advantages of this pulse sequence over conventional sequences with rectilinear k-space trajectories are the reduced number of refocusing RF pulses and the low diffusion-induced signal attenuation during the echo train. Also, since all of the hyperpolarized magnetization is converted to transverse magnetization by the excitation RF pulse, the signal-to-noise ratio for the resulting images is maximized.

For MR imaging, the rabbits were anesthetized with a mixture of xylazine 1 mg/kg and ketamine 0.1 mg/kg and intubated with an endotracheal tube. Imaging was performed in the eighth week after elastase treatment began. The protocol was approved by the Institutional Animal Care and Use Committee. Rabbits were ventilated with 60 cc of natural abundance (27% xenon-129) or isotopically enriched (85% xenon-129) xenon gas, polarized to approximately 10-15% via spin exchange with an optically pumped rubidium vapor (Model IGI 9600Xe Xenon Polarizer, MITI, Durham, N.C.).

Figure 2:
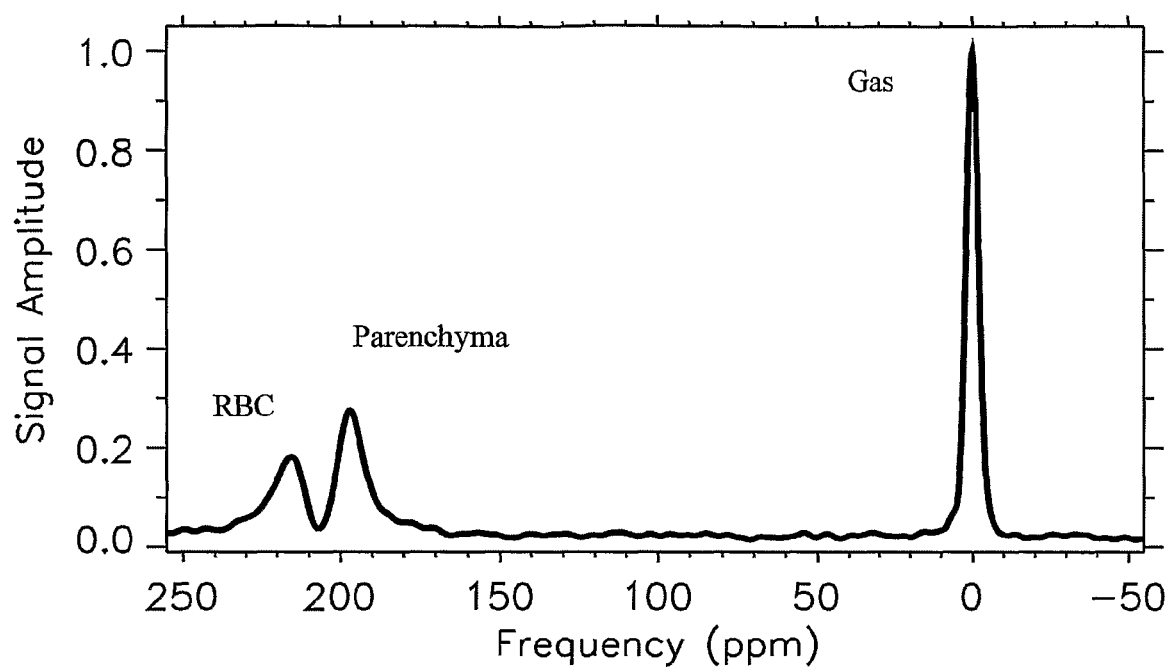
FIG. 2 provides a plot that graphically depicts a representative hyperpolarized xenon-129 NMR spectrum from the chest of a canine, demonstrating, for example, the major resonances that can be detected.

For the experimental conditions described above, FIG. 2 shows a representative xenon-129 NMR spectrum from the canine chest (spectra from the rabbit chest are qualitatively equivalent). Three prominent spectral peaks are observed, attributed to (from left to right) dissolved-phase xenon in red blood cells and the lung parenchyma, and gas-phase xenon in the lung air spaces. Note that this spectrum was acquired following a 900-ms, Gaussian-shaped 90° RF pulse with a center frequency at approximately 200 ppm in FIG. 2. The flip angle at the gas-phase frequency (0 ppm in FIG. 2) was thus less than 1°, indicating that the gas-phase reservoir is substantially larger than the dissolved-phase reservoirs. The large peak at 0 ppm is the gas in the lung, while the peaks at 197 ppm and 212 ppm are believed to arise from xenon-129 dissolved in the lung parenchyma and bound to red blood cells (RBC), respectively.

As a specific implementation of the general three-step process outlined above, the following experiment was performed immediately following the inhalation of 60 cc of hyperpolarized xenon by the rabbits. Step 1: A 90° excitation RF pulse centered at 0 ppm converted the available gas-phase longitudinal magnetization into transverse magnetization. Step 2: During a 288-ms delay between the excitation RF pulse and the acquisition of the central region of k space, xenon-129 atoms from the alveolar gas phase entered the lung parenchyma and experienced a shift in resonance frequency of about 200 ppm. At 1.5 Tesla this translates to a 3.5 kHz frequency difference, which fully dephases the transverse magnetization of the atoms inside the tissue with respect to the gas phase within about 300 µs. Therefore, the dephasing can be considered to be almost instantaneous upon entering the dissolved phase on the time scale of the experiment. The length of the delay (288 ms) ensures that a sufficiently large fraction of the gas-phase atoms had a chance to enter the lung tissue and return to the gas phase. Step 3: Data for an MR image were acquired by using a spin-echo-train pulse sequence with a circular k-space trajectory that consisted of 32 concentric rings along which 256 data points were sampled. The data were gridded onto a subsampled 64×64 matrix and Fourier transformed. The following sequence parameters were used: effective-TE 288 ms, field-of-view 400 mm, slice thickness 100-mm, acquisition time 0.3 seconds. The acquisition order of the circles was outside-in (i.e., from the edges of k space inward) for maximum exchange weighting and resolution. For this pulse-sequence type, steps 2 and 3 actually occur in parallel. However, this is not a prerequisite for the invention.

Figure 3:
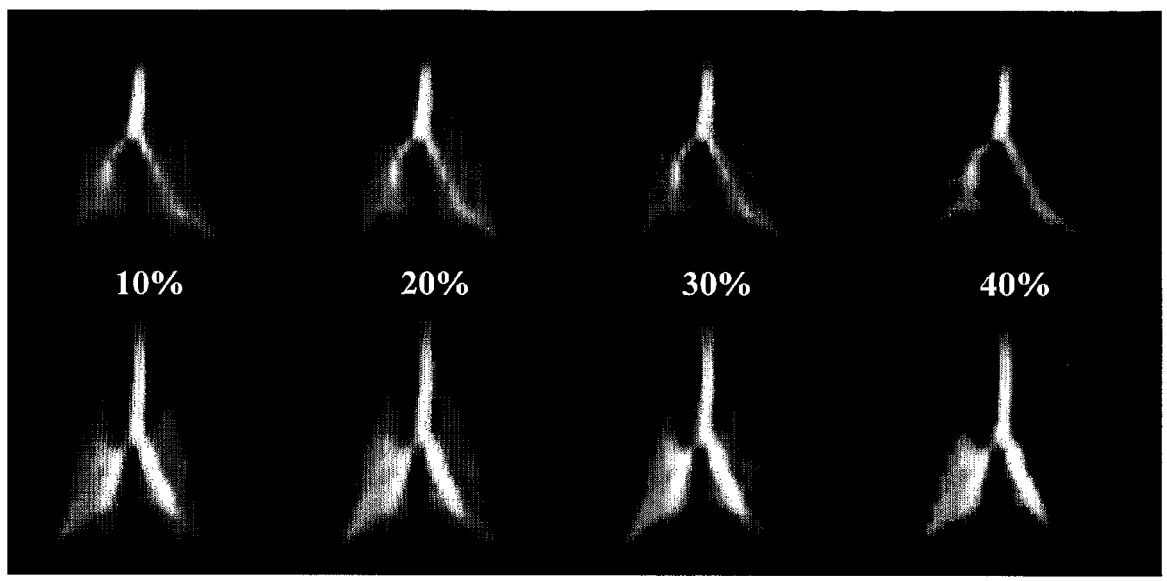
FIG. 3 shows rabbit lung images, acquired with an implementation of an embodiment of the present invention, for four different signal threshold levels. The upper row is from a healthy rabbit while the right lung of the rabbit shown in the lower row had been treated with elastase to induce regional lung-tissue destruction.

FIG. 3 illustrates how the exchange-weighted contrast can be used to detect regions of lung-tissue destruction, for instance, in emphysematous lung. Provided is the signal intensity at four different threshold levels for a healthy (upper row) and emphysematous (bottom row) lung. Since the presence of lung parenchyma is essential for gas exchange and the subsequent dephasing of the transverse magnetization, regions with a reduced tissue density appear brighter in an exchange-weighted image. By varying the threshold for the pixel intensities that are displayed, areas of tissue breakdown are highlighted (lower row). No such regions are enhanced in normal lung (upper row). The lung region detected as emphysematous by our invention was in excellent agreement with independently acquired apparent diffusion coefficient (ADC) maps that showed a concomitant ADC elevation. All pixel values below the indicated percentage of the maximum intensity are set to zero. The residual signal intensity outside the major airways in the emphysematous lung at a 40 percent threshold outlines the region with the most lung tissue destruction.

The various embodiments of the present invention might prove particularly useful at lower magnetic field strengths (e.g., 0.15 Tesla) where XTC MRI does not work well due to the reduced frequency separation between the target and reference compartments. Also, the image contrast from our invention will be a function of the magnetic field strength. At high field strengths, the frequency difference between the target and the reference compartments is so large that dephasing occurs even for brief exposures of the gas-phase atoms to the target compartments. The dephasing will therefore be heavily weighted by the local surface-to-volume ratio. At lower field strengths, on the other hand, only atoms that spend substantial periods of time in the target compartments will experience significant dephasing. Thus, the image contrast will then reflect information about deeper layers of the target compartments as well. In this context the magnetic field strength would be considered "high" when the time to accumulate a phase difference of $2\pi$ between the transverse magnetization in the reference compartment and that in the target compartments is small compared to the time it takes for the xenon-129 atoms to diffuse across the target compartments, while it would be considered "low" for the opposite scenario.

The following references as cited throughout this document are hereby incorporated by reference herein in their entirety:

1. Albert M S, Cates G D, Driehuys B, et al. Biological magnetic resonance imaging using laser-polarized $^{129}$Xe. Nature 1994; 370:199-201.
2. Song Y Q, Gaede H C, Pietrass T, et al. Spin-polarized $^{129}$Xe gas imaging of materials. J Magn Reson 1995; A115: 127-130.
3. Abraham M H, Kamlet M J, Taft R W, Doherty R M, Weathersby P K. Solubility properties in polymers and biological media. 2. The correlation and prediction of the solubilities of nonelectrolytes in biological tissues and fluids. J Med Chemistry 1985; 28:865-870.
4. Miller K W, Reo N V, Uiterkamp A J M S, Stengle D P, Stengle T R, Williamson K L. Xenon NMR: chemical shifts of a general anesthetic in common solvents, proteins, and membranes. Proc Natl Acad Sci USA 1981; 78:4946-4949.
5. Ruppert K, Brookeman J R, Hagspiel K D, Mugler J P III. Probing lung physiology with xenon polarization transfer contrast (XTC). Magn Reson Med 2000; 44:349-357.
6. Ruppert K, Mata J F, Brookeman J R, Hagspiel K D, Mugler J P III. Exploring lung function with hyperpolarized $^{129}$Xe nuclear magnetic resonance. Magn Reson Med 2004; 51:676-687.
7. Walker T G, Happer W. Spin-exchange optical pumping of noble gas nuclei. Rev Mod Phys 1997;69:629-642.

In summary, the various embodiments of the present invention method and system provide, among other things, the means for using hyperpolarized xenon-129 as a probe to non-invasively and non-destructively characterize important properties of certain structures or materials into which hyperpolarized xenon-129 can be introduced and wherein said xenon exists in two or more chemically-shifted states that are in exchange. High-resolution MR images can be generated in a fraction of a second wherein the associated signal intensities reflect material properties that characterize the gas exchange among the different states. For example, in the human or animal lung, the invention can exploit the differences in gas-exchange characteristics between healthy and diseased lung tissue to generate high-resolution, high signal-to-noise cross-sectional MR images that permit non-invasive regional detection of variations in lung tissue structure with a combination of spatial and temporal resolution that is unmatched by any current imaging modality.

For example, an embodiment of the present invention method and system may be implemented in two fields: medicine and materials science (but not limited thereto). In the medical area, the present invention shall be important for the study and characterization of certain properties of the healthy and diseased lung. Various embodiments of the present invention provide the ability to measure properties such as the lung-tissue volume and surface-to-volume ratio. In a more general sense, our invention permits a non-invasive measurement of the gas exchange characteristics of the lung with a combination of spatial resolution, temporal resolution and signal-to-noise ratio that is unmatched by any current imaging modality. Since gas exchange is the primary physiological function of the lung, one would expect that the ability to characterize the gas-exchange properties of the lung in this way would be of substantial importance. More specifically, the invention may be useful in certain pulmonary diseases for diagnosis, for following the response to therapy, and for better understanding the pathophysiology of these diseases. Thus, some embodiments of the invention shall be a valuable tool for pharmaceutical companies to help in the formulation and quantitative evaluation of new respiratory drugs. In addition, some embodiments of the present invention shall be useful for better understanding the physiology of the healthy lung, including the changes that occur with aging and smoking.

In the materials science area, embodiments of the present invention method and system shall provide the means to nondestructively determine properties of certain materials.

An advantage of the various embodiments of the present invention method and system includes, but not limited thereto, is that it will permit certain gas exchange characteristics of the healthy or diseased lung to be measured in a non-invasive fashion with high signal-to-noise and a combination of spatial and temporal resolution that is unmatched by any current imaging modality.

Practice of various embodiments will be still more fully understood from the following examples, which are presented herein for illustration only and should not be construed as limiting the invention in any way.

Example No. 1

An aspect of an embodiment includes a method of characterizing properties of a certain structure or material, wherein the structure or material have at least one compartment therein. At least one of the compartments define at least one reference compartment, and the structure or material also has at least one other compartment, which defines at least one target compartment. The method comprises: a) introducing hyperpolarized xenon-129 gas in the structure or material and placing the structure or material in a NMR or MRI system; b) creating transverse magnetization from the hyperpolarized xenon-129 gas in at least one of the reference compartments that has a corresponding chemical shift; and c) leaving the NMR or MRI system unperturbed for an appropriately chosen delay time. The delay time may be chosen such that a sufficiently large quantity of xenon-129 atoms enters the target compartments from the reference compartment. The xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process. Upon return to the reference compartment the transverse magnetization is dephased relative to that which remained in the reference compartment and this transverse magnetization from the target compartments thus makes a reduced contribution to the coherent gas-phase signal, which results in a reduced net signal from the alveolar gas-phase transverse magnetization compared to the situation wherein there is relatively reduced or no xenon exchange between the reference and target compartments. The method may also include measuring the signal from hyperpolarized xenon-129 in the reference compartment.

Still referring to the exemplary method of characterizing properties of a certain structure or material, the duration of the delay time may be chosen based on at least one of: external magnetic field strength; exchange rate between the reference compartment and target compartments; residence time of xenon-129 within the target compartment(s); and xenon-129 diffusion properties in the target compartment(s). In addition, the measured signal from the reference compartment reflects the degree of dephasing of the xenon-129 transverse magnetization inside the target compartments with respect to the reference compartment of step (c) above, and the time constants, partition coefficients and geometrical factors characterizing the xenon exchange between the reference and target compartments. Moreover, the information that the measured signal reflects depends on the difference in resonance frequency between the reference and the target compartments. Additionally, the information comprises volume of material in which the xenon dissolves. Also, the signal measurement from hyperpolarized xenon-129 in the reference compartment may also reflect other independent processes. Some of the other independent processes may comprise at least one of T1 and T2 relaxation and diffusion of xenon in the reference compartment, wherein the method further comprises selecting an appropriately designed pulse sequence. For example, the selected pulse sequence and the chosen delay time ensure that contributions to the measured signal from the other independent processes are insignificant relative to that from the exchange process. The reference compartment may comprise at least a portion of the lung, wherein at least a portion of the lung is from an animal or human. Also, the lung may be in vivo or excised. Further, the target compartment comprises at least a portion of a least one of the lung parenchyma and lung alveolar capillary bed. Further, the reference compartment and the target compartment may comprise at least a portion of an organ or an animal or human. The characterizing properties may provide means to nondestructively determine properties of certain materials. The measured signal reflects the signal from all Xe129 nuclei within the lung. Also, the measured signal may reflect the signal from Xe129 nuclei within one or more selected sub-volumes within the whole of the lung, wherein each sub-volume may correspond to a planar slice of lung tissue, a column of lung tissue, or some arbitrarily-shaped volume of lung tissue. Moreover, at least one magnetic field gradient pulse may be applied for at least one of before and during the process of acquiring of the measured signal in any manner consistent with imaging pulse sequences known in the art to permit an exchange-weighted magnetic resonance image, resolved in one, two or three spatial dimensions, to be calculated. Additionally, the exchange-weighted magnetic resonance images may be acquired corresponding to one or more spatial locations.

Example No. 2

An aspect of an embodiment includes a system for characterizing properties of a certain structure or material, wherein the structure or material may have at least one compartment therein. At least one of the compartments define at least one reference compartment, and the structure or material also has at least one other compartment therein, which defines at least one target compartment. Accordingly, the system comprises an NMR or MRI system where it is adapted to allow the introduction of hyperpolarized xenon-129 gas in the structure or material and placement of the structure or material in the NMR or MRI system. Additionally, the NMR or MRI system may be adapted to allow creation of a transverse magnetization from the hyperpolarized xenon-129 gas in at least one of the reference compartments that has a corresponding chemical shift. Further, the NMR or MRI system may be adapted to allow its system to be unperturbed for an appropriately chosen delay time. The delay time may be chosen such that a sufficiently large quantity of xenon-129 atoms enter the target compartments from the reference compartment, the xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process. Further, upon return to the reference compartment the transverse magnetization is dephased relative to that which remained in the reference compartment and this transverse magnetization from the target compartments thus makes a reduced contribution to the coherent gas-phase signal, which results in a reduced net signal from the alveolar gas-phase transverse magnetization compared to the situation wherein there is relatively reduced or no xenon exchange between the reference and target compartments. Still further, the NMR or MRI system may be adapted to allow for the measurement of the signal from hyperpolarized xenon-129 in the reference compartment.

Still referring to the exemplary system the duration of the delay time may be chosen based on at least one of: external magnetic field strength, exchange rate between the reference compartment and target compartments, residence time of xenon-129 within the target compartment(s) and xenon-129 diffusion properties in the target compartment(s). The measured signal from the reference compartment reflects the degree of dephasing of the xenon-129 transverse magnetization inside the target compartments with respect to the reference compartment, and the time constants, partition coefficients and geometrical factors characterizing the xenon exchange between the reference and target compartments. The information that the measured signal reflects depends on the difference in resonance frequency between the reference and the target compartments. Also, the information may comprise volume of material in which the xenon dissolves. Further, the measurement of the signal from hyperpolarized xenon-129 in the reference compartment may also reflect other independent processes. Such other independent processes may comprise at least one of T1 and T2 relaxation and diffusion of xenon in the reference compartment, wherein the NMR or MRI system may be adapted to further comprise selecting an appropriately designed pulse sequence. The selected pulse sequence and the chosen delay time ensure that contributions to the measured signal from the other independent processes are insignificant relative to that from the exchange process. Moreover, the reference compartment may comprise at least a portion of the lung, wherein at least a portion of the lung is from an animal or human. The lung may be in vivo or excised. Still yet, the target compartment may comprise at least a portion of a least one of lung parenchyma and lung alveolar capillary bed. The reference compartment and the target compartment may comprise at least a portion of an organ or an animal or human. Moreover, the characterizing properties provide means to nondestructively determine properties of certain materials, wherein the measured signal reflects the signal from all Xe129 nuclei within the lung. Also, the measured signal reflects the signal from Xe129 nuclei within one or more selected sub-volumes within the whole of the lung, wherein each sub-volume may correspond to a planar slice of lung tissue, a column of lung tissue, or some arbitrarily-shaped volume of lung tissue. Additionally, at least one magnetic field gradient pulse may be applied for at least one of before and during the acquisition of the measured signal in any manner consistent with imaging pulse sequences known in the art to permit an exchange-weighted magnetic resonance image, resolved in one, two or three spatial dimensions, to be calculated. Finally, the exchange-weighted magnetic resonance may be acquired corresponding to one or more spatial locations.

It should be understood that while the method described was presented with a certain ordering of the steps, it is not our intent to in any way limit the present invention to a specific step order. It should be appreciated that the various steps can be performed in different orders, for example, step numbers 1-3 as enumerated in this document. Further, we have described herein the novel features of the present invention, and it should be understood that we have not included details well known by those of skill in the art, such as the design and operation of a MR imaging system.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, section, abstract, drawing figure, etc.) of this application, unless clearly specified to the contrary, there is no requirement for any particular described or illustrated activity or element, any particular sequence of such activities, any particular size, speed, dimension or frequency, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive.

We claim:

1. A method of characterizing properties of a lung, the lung having at least one compartment therein, said at least one compartment defining at least one reference compartment and the lung having at least one other compartment therein, said at least one other compartment defining at least one target compartment, said method comprising:
   a) introducing hyperpolarized xenon-129 gas in the lung and
   placing the lung in a NMR or MRI system;
   b) creating transverse magnetization from the hyperpolarized xenon-129 gas in at least one of the reference compartments that has a corresponding chemical shift;
   c) leaving the NMR or MRI system unperturbed for an appropriately chosen delay time, wherein
     said delay time is chosen such that a sufficiently large quantity of xenon-129 atoms enter the target compartments from the reference compartment, the xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process, and
     upon return to the reference compartment the transverse magnetization is dephased relative to that which remained in the reference compartment and this transverse magnetization from the target compartments thus makes a reduced contribution to the coherent gas-phase signal, which results in a reduced net signal from alveolar gas-phase transverse magnetization compared to the situation wherein there is relatively reduced or no xenon exchange between the reference and target compartments;
   d) measuring said signal from hyperpolarized xenon-129 in the reference compartment; and
   e) processing said signal from hyperpolarized xenon-129 in the reference compartment to determine a difference in at least one gas-exchange property of said lung among at least two spatial locations;
   wherein the target compartment comprises at least a portion of a least one of lung parenchyma and lung alveolar capillary bed, and wherein the reference compartment comprises at least a portion of the lung.

2. The method of claim 1, wherein duration of said delay time is chosen based on at least one of:
   external magnetic field strength, exchange rate between the reference compartment and target compartments, residence time of xenon-129 within the target compartment(s) and xenon-129 diffusion properties in the target compartment(s).

3. The method of claim 1, wherein said measured signal from the reference compartment reflects the degree of dephasing of the xenon-129 transverse magnetization inside the target compartments with respect to the reference compartment of step (c), and the time constants, partition coefficients and geometrical factors characterizing the xenon exchange between the reference and target compartments.

4. The method of claim 3, wherein information that the measured signal reflects depends on the difference in resonance frequency between the reference and the target compartments.

5. The method of claim 4, wherein said information comprises volume of material in which the xenon dissolves.

6. The method of claim 1, wherein said signal from hyperpolarized xenon-129 in the reference compartment at step (d) may also reflect other independent processes.

7. The method of claim 6, wherein said other independent processes comprise at least one of T1 and T2 relaxation and diffusion of xenon in the reference compartment.

8. The method of claim 7, further comprising selecting an appropriately designed pulse sequence.

9. The method of claim 8, wherein said selected pulse sequence and said chosen delay time ensures that contributions to said measured signal from said other independent processes are insignificant relative to that from said exchange process.

10. The method of claim 1, wherein the at least a portion of the lung is from an animal or human.

11. The method of claim 10, wherein the lung may be in vivo or excised.

12. The method of claim 1, wherein the characterizing properties provide means to nondestructively determine properties of certain materials.

13. The method of claim 1, wherein said measured signal reflects the signal from all Xe129 nuclei within the lung.

14. The method of claim 1, wherein said measured signal reflects the signal from Xe129 nuclei within one or more selected sub-volumes within the whole of the lung, wherein each said sub-volume may correspond to a planar slice of lung tissue, a column of lung tissue, or some arbitrarily-shaped volume of lung tissue.

15. The method of claim 1, wherein at least one magnetic field gradient pulse is applied for at least one of before and during the acquiring of said measured signal in any manner consistent with imaging pulse sequences known in the art to permit an exchange-weighted magnetic resonance image, resolved in one, two or three spatial dimensions, to be calculated.

16. The method of claim 15, wherein exchange-weighted magnetic resonance images are acquired corresponding to one or more spatial locations.

17. The method of claim 1, wherein in step (c) said transverse magnetization is manipulated by at least one of at least one suitably balanced magnetic field gradient and at least one refocusing RF pulse.

18. A system for characterizing properties of a lung, the lung having at least one compartment therein, said at least one compartment defining at least one reference compartment and the lung having at least one other compartment therein, said at least one other compartment defining at least one target compartment, said system comprising:
   a) an NMR or MRI system adapted to allow:
      introduction of hyperpolarized xenon-129 gas in the lung and
      placement of the lung in an NMR or MRI system;
   b) said NMR or MRI system adapted to allow:
      creation of a transverse magnetization from the hyperpolarized xenon-129 gas in at least one of the reference compartments that has a corresponding chemical shift;
   c) said NMR or MRI system adapted to allow:
      leaving said NMR or MRI system substantially unperturbed for an appropriately chosen delay time, wherein
      said delay time is chosen such that a sufficiently large quantity of xenon-129 atoms enter the target compartments from the reference compartment, the xenon-129 transverse magnetization in the target compartments acquires a relatively large range of phase shifts with respect to the transverse magnetization in the reference compartment, and xenon-129 atoms in the target compartments diffuse back to the compartment boundary where they exchange with the reference compartment, thereby defining an exchange process, and
      upon return to the reference compartment the transverse magnetization is dephased relative to that which remained in the reference compartment and this transverse magnetization from the target compartments thus makes a reduced contribution to the coherent gas-phase signal, which results in a reduced net signal from alveolar gas-phase transverse magnetization compared to the situation wherein there is relatively reduced or no xenon exchange between the reference and target compartments;
   d) said NMR or MRI system adapted to allow:
      measurement of said signal from hyperpolarized xenon-129 in the reference compartment; and
   e) said NMR or MRI system adapted to allow:
      processing of said signal from hyperpolarized xenon-129 in the reference compartment to determine a difference in at least one gas-exchange property of lung among at least two spatial locations;
   wherein the target compartment comprises at least a portion of a least one of lung parenchyma and lung alveolar capillary bed, and wherein the reference compartment comprises at least a portion of the lung.

19. The system of claim 18, wherein duration of said delay time is chosen based on at least one of:
   external magnetic field strength, exchange rate between the reference and target compartments, residence time of xenon-129 within the target compartment(s) and xenon-129 diffusion properties in the target compartment(s).

20. The system of claim 18, wherein said measured signal from the reference compartment reflects the degree of dephasing of the xenon-129 transverse magnetization inside the target compartments with respect to the reference compartment of element (c), and the time constants, partition coefficients and geometrical factors characterizing the xenon exchange between the reference and target compartments.

21. The system of claim 20, wherein information that the measured signal reflects depends on the difference in resonance frequency between the reference and the target compartments.

22. The system of claim 21, wherein said information comprises volume of material in which the xenon dissolves.

23. The system of claim 18, wherein said measurement of said signal from hyperpolarized xenon-129 in the reference compartment may also reflect other independent processes.

24. The system of claim 23, wherein said other independent processes comprise at least one of T1 and T2 relaxation and diffusion of xenon in the reference compartment.

25. The system of claim 24, wherein said NMR or MRI system is adapted to further comprise selecting an appropriately designed pulse sequence.

26. The system of claim 25, wherein said selected pulse sequence and said chosen delay time ensures that contributions to said measured signal from said other independent processes are insignificant relative to that from said exchange process.

27. The system of claim 18, wherein the at least a portion of the lung is from an animal or human.

28. The system of claim 27, wherein the lung may be in vivo or excised.

29. The system of claim 18, wherein the characterizing properties provide means to nondestructively determine properties of certain materials.

30. The system of claim 18, wherein said measured signal reflects the signal from all Xe129 nuclei within the lung.

31. The system of claim 18, wherein said measured signal reflects the signal from Xe129 nuclei within one or more selected sub-volumes within the whole of the lung, wherein each said sub-volume may correspond to a planar slice of lung tissue, a column of lung tissue, or some arbitrarily-shaped volume of lung tissue.

32. The system of claim 18, wherein at least one magnetic field gradient pulse is applied for at least one of before and during the acquisition of said measured signal in any manner consistent with imaging pulse sequences known in the art to permit an exchange-weighted magnetic resonance image, resolved in one, two or three spatial dimensions, to be calculated.

33. The system of claim 32, wherein exchange-weighted magnetic resonance images are acquired corresponding to one or more spatial locations.

34. The system of claim 18, wherein in step (c) said transverse magnetization is manipulated by at least one of at least one suitably balanced magnetic field gradient and at least one refocusing RF pulse.

* * * * *